(12) United States Patent
Andersen et al.

(10) Patent No.: US 7,263,255 B2
(45) Date of Patent: Aug. 28, 2007

(54) SYSTEM, METHOD AND APPARATUS FOR PROVIDING UNIFORM ILLUMINATION

(75) Inventors: Dan E. Andersen, Menlo Park, CA (US); David G. Angeley, Charlottesville, VA (US); Michael W. Wiltberger, Santa Clara, CA (US)

(73) Assignee: Lumenis Inc., Santa Clara, CA (US)

( * ) Notice: Subject to any disclaimer, the term of this patent is extended or adjusted under 35 U.S.C. 154(b) by 326 days.

(21) Appl. No.: 10/408,783

(22) Filed: Apr. 8, 2003

(65) Prior Publication Data

US 2003/0231827 A1 Dec. 18, 2003

Related U.S. Application Data

(60) Provisional application No. 60/370,217, filed on Apr. 8, 2002.

(51) Int. Cl.
*G02B 6/26* (2006.01)
(52) U.S. Cl. .......................................... 385/31; 385/15
(58) Field of Classification Search ................. 385/15, 385/31; 359/196–226
See application file for complete search history.

(56) References Cited

U.S. PATENT DOCUMENTS

| | | | |
|---|---|---|---|
| 4,047,795 A * | 9/1977 | Hughes et al. ................ 385/37 |
| 4,475,027 A | 10/1984 | Pressley | |
| 4,534,615 A | 8/1985 | Iwasaki | |
| 4,653,495 A | 3/1987 | Nanaumi | |
| 4,718,416 A | 1/1988 | Nanaumi | |
| 4,734,550 A | 3/1988 | Imamura et al. | |
| 4,807,963 A | 2/1989 | Iwasaki | |
| 4,941,734 A | 7/1990 | Williams et al. | |
| 5,336,216 A | 8/1994 | Dewey | |
| 5,336,217 A | 8/1994 | Buys et al. | |
| 5,411,502 A | 5/1995 | Zair | |
| 5,428,699 A | 6/1995 | Pon | |
| 5,474,549 A | 12/1995 | Ortiz et al. | |
| 5,633,695 A | 5/1997 | Feke et al. | |

(Continued)

FOREIGN PATENT DOCUMENTS

JP          63-137120         6/1988

(Continued)

OTHER PUBLICATIONS

Sterenborg, HJCM, et al. "Photodynamic therapy with pulsed light sources:a theoretical analysis" Physics in medicine and Biology, 41 (1996) pp. 835-849.

(Continued)

*Primary Examiner*—Jennifer Doan
(74) *Attorney, Agent, or Firm*—Pearl Cohen Zedek Latzer LLP

(57) ABSTRACT

An apparatus and method may provide uniform illumination on the retina using scanned continuous wave laser sources by making use of waveguides with regular shaped cross sections. Some embodiments of the present invention may provide illumination uniformity for selected spots and/or whole target scans, and may provide for constant dwell times every point of the scanned beam. Furthermore, the non-uniformities caused by starting and stopping scans may be eliminated by, for example, clipping-off both the beginning and end of the scan with a hard aperture. A modulator may be provided, enabling uniform irradiation of selected target areas.

5 Claims, 8 Drawing Sheets

U.S. PATENT DOCUMENTS

| | | | |
|---|---|---|---|
| 5,743,902 | A | 4/1998 | Trost |
| 5,786,924 | A | 7/1998 | Black et al. |
| 5,860,968 | A | 1/1999 | Wojcik et al. |
| 5,997,141 | A | 12/1999 | Heacock |
| 6,149,644 | A | 11/2000 | Xie |
| 6,186,628 | B1 * | 2/2001 | Van de Velde ............... 351/205 |
| 6,193,710 | B1 | 2/2001 | Lemberg |
| 6,267,756 | B1 | 7/2001 | Feuerstein et al. |
| 6,413,268 | B1 | 7/2002 | Hartman |
| 6,537,270 | B1 | 3/2003 | Elbrecht et al. |
| 6,648,876 | B2 | 11/2003 | Murakami |
| 6,676,654 | B1 | 1/2004 | Balle-Petersen et al. |
| 2001/0001118 | A1 | 5/2001 | Asah et al. |
| 2002/0138071 | A1 | 9/2002 | Angeley et al. |
| 2002/0161357 | A1 | 10/2002 | Anderson et al. |
| 2005/0049582 | A1 | 3/2005 | DeBenedictis et al. |
| 2006/0161145 | A1 * | 7/2006 | Lin et al. ....................... 606/17 |

FOREIGN PATENT DOCUMENTS

| | | |
|---|---|---|
| JP | 2-252453 | 10/1990 |
| WO | WO95/18984 | 7/1995 |
| WO | WO99/58047 | 11/1999 |
| WO | WO 00/10049 | 2/2000 |
| WO | WO 01/91661 | 12/2001 |
| WO | WO 02/076318 | 10/2002 |

OTHER PUBLICATIONS

Roider, J. "Laser treatment of retinal diseases by subthreashold laser effects." Seminars in Ophthalmology, (Mar. 14, 1999) pp. 19-26.

Gabel, VP, et al. "Visible and near infrared light absorption in pigment epithelium and choriod" Congress Series: XXIII Clinicum Ophthalmologicum, 450 (1978).

D. Dewey, "Corneal and Retinal Energy Density with various laser beam delivery systems and contact lenses" Ophthalmic Technologies, SPIE vol. 1423. 105-116. 1991.

R. Brinkman, et al. "Origin of Retinal Pigment Epithelium Cell Damage by Pulsed Laser Irradiance in the Nanosecond to Microsecond Time Regimen" Lasers Surg. Med. 27:451-464, 2000.

Kurt G. Klavuhn, "Illumination Geometry: The Importance of Laser Beam Special Characteristics", Coherent Medical Group Laser Hair Removal Technical Note No. 2: Feb. 2000, pp. 1-8.

John F. Black et al., "Cooperative Phenomena in Two-Pulse, Two Color Laser Photocoagulation of Cutaneous Blood Vessels", Proc SPIE 4244A-02, May 2001.

John F. Black et al., "Time-domain Optical and Thermal Properties of Blood Undergoing Laser Photocoagulation", Proc SPIE 4257A-44, Jul. 2001, pp. 341-354.

S.L. Jacques, "The Role of Skin Optics in Diagnostic and Therapeutic uses of Lasers", Lasers in Dermatology Proc of International Symposium, Ulm Sep. 26, 1989, pp. 1-21.

* cited by examiner

Standard windowing aperture

"Gated" windowing aperture

SYSTEM, METHOD AND APPARATUS FOR PROVIDING UNIFORM ILLUMINATION

CROSS REFERENCE TO RELATED APPLICATIONS

This application claims priority from U.S. Provisional Patent Application No. 60/370,217, filed Apr. 8, 2002, entitled "METHODS AND APPARATUS FOR MICRO-PHOTOCOAGULATION" which is incorporated in its entirety herein by reference.

FIELD OF THE INVENTION

The present invention relates to methods and devices useful in laser surgical and diagnostic techniques. Specifically, embodiments of the present invention relate to systems, methods and apparatuses that provide uniform illumination on the retina.

BACKGROUND OF THE INVENTION

Laser-based tools have become the standard for treating and diagnosing quite a number of ophthalmic conditions, such as the complications associated with diabetes, glaucoma, and aging. Lasers are also used, amongst other things, to seal retinal holes and detachments by welding them back together. One element of these types of laser surgery is the use of the Retinal Pigmented Epithelium (RPE) as a target for absorbing the laser energy. The RPE is a single cellular layer that separates the photoreceptors from their blood supply in the choroid. Retinal laser surgery can be classified into two distinct types of treatment. Some treatments rely on thermal damage to the neuroretinal layer (such as retinal welding), and others seek to minimize damage to the neuroretina (such as microphotocoagulation, or selective RPE therapy (SRT)). However, both these treatment types are often typically referred to simply as "photocoagulation" (PC).

PhotoCoagulation (PC) has been established as a standard for treating a wide variety of retinal disorders, for example, in the condition known as proliferative diabetic retinopathy. In this condition, abnormal new blood vessels develop from the optic nerve area or elsewhere in the retina and frequently lead to severe visual loss from hemorrhage and other complications. PC is typically applied extensively from near the optic nerve margin to the periphery of the retina, while sparing the central macular area, which has the highest density of photoreceptors, and is functionally important for seeing detail.

In conventional PC, the lightpulses used to implement the PhotoCoagulation are usually of the order of 50-100 ms with fluences in the order of ~4 J/mm$^2$. These parameters allow for considerable heat flow from the melanosomes (which are the pigmented organelles that contain the RPE's melanin) during irradiation. This heat flow can often damage the surrounding structures, such as the photoreceptors. This is undesirable, as amongst other things, it may lower one's visual acuity by creating blindspots known as "scotomas".

More recently a new approach to PC therapy has emerged, which is often referred to as "MicroPhotoCoagulatian," (MPC) or "Selective RPE Treatment" (SRT). The main difference between early SRT techniques and PC is that SRT typically uses laser pulses of short duration (for example, $10^{-6}$s) so that the heat generated by their absorption in the RPE generates high temperatures only in the melanosomes, while still instigating a generalized retinal wound healing response.

Original MicroPhotoCoagulation research includes work by Birgruber, Roider et al. in Lubeck, Germany, using pulsed lasers delivering relatively large spots. These pulses, however, are typically expensive to manufacture.

Further work on MicroPhotoCoagulation has been done by Lin et al. at the Wellman Laboratories of Photomedicine in Boston, using a fiber-coupled, scanned continuous wave (CW) 532 nm laser with fluences of ~0.3 J/cm$^2$ that is delivered with microsecond dwell times. This method, however, delivers round spots that may result in uneven scanning of the target tissue due to the difference in dwell times across the beam.

SUMMARY OF THE INVENTION

There is provided, in accordance with an embodiment of the present invention, an apparatus, system, and method for providing uniform illumination to all or selected points in target tissue, such as the retina. Provision of such illumination may enable treatment dosimetry and uniform dwell times on tissue, such as RPE cells, for example. According to some embodiments of the present invention, both cumulative and immediately uniform fluence distributions may be provided using a scanned continuous wave (CW) laser.

In accordance with some embodiments of the present invention, uniform fluence distributions may be scanned using appropriate time constants, such that every target point or spot may be illuminated with a moving beam for a specific time. According to some embodiments of the present invention, raster scanning may be implemented to transmit the beam(s) to the target cells or selected target cells.

In accordance with some embodiments of the present invention, uniform dosimetry of target points or spots may be enabled by using waveguides with regularly shaped cross sections that may generate regularly shaped light beams.

In accordance with some embodiments of the present invention, uniform dosimetry of target points or spots may be enabled by using regular shaped waveguides with smoothed or clipped edges.

In accordance with some embodiments of the present invention, instantaneous uniform illumination may be implemented using continuous wave (CW) laser scanning through waveguides with regularly shaped cross sections, the beams from which may fit together to precisely cover the target surface. According to some embodiments of the present invention, a modulator may be provided, which may enable selection of target areas for irradiation.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
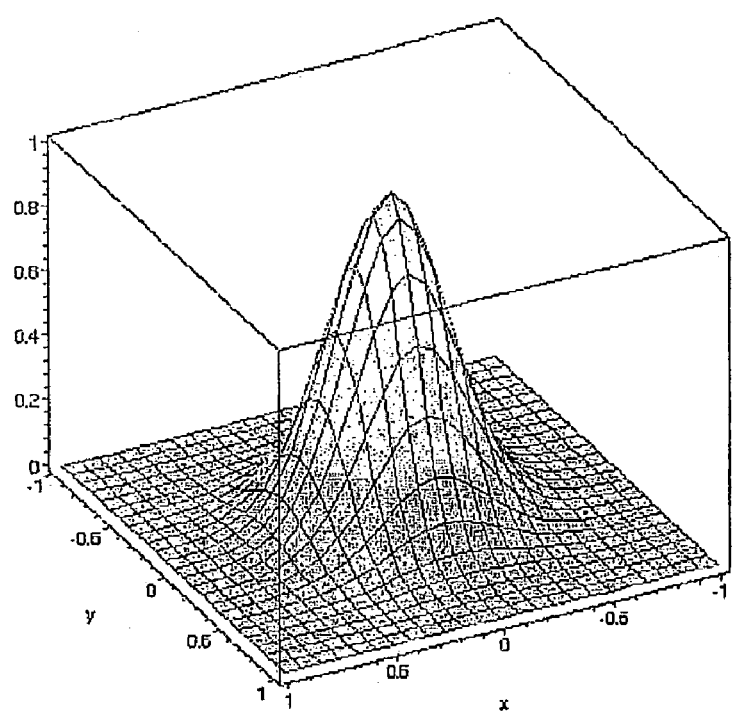
FIG. 1 illustrates a typical 3-dimensional Gaussian distribution, according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In the following detailed description, numerous specific details are set forth in order to provide a thorough understanding of the present invention. However, it will be understood by those skilled in the art that the present invention may be practiced without these specific details.

The word "waveguides" as used hereinafter may encompass fiber optic, glass, plastic or any other elements for channeling light energy. The expression "regular shapes", "geometric shapes" and the like, as used hereinafter, may refer to optical waveguides with cross-sectional geometries that have equidistant edges as defined by a scan direction. When such waveguides are scanned they may produce nominally equal irradiance at every point in the scan. These waveguides may encompass various, regular, symmetric, bi-symmetric forms and any other forms, such as, for example, squares, rectangles, and the like.

Embodiments of the present invention enable the provision of uniform illumination using continuous wave (CW) laser sources. The apparatus and method, according to some embodiments of the present invention, may use optical waveguides with cross-sectional geometries that have equidistant edges as defined by a scan direction. This method may use the delivered light efficiently, and may allow for identical dwell times for all points in the scanned image. This method may enable the implementation of uniform light illumination in various techniques including standard PhotoCoagulation (PC), MicroPhotoCoagulation (MPC), photodynamic therapy and illumination for imaging etc.

According to some embodiments of the present invention, a far field laser beam intensity profile may be defined by, for example, a 3-dimensional Gaussian distribution, a normalized example of which is given by the following equation:

$$G = e^{-2\frac{r^2}{w^2}}$$

where w is the characteristic $e^{-2}$ width of the distribution, and r is the distance from the beam's center.

The Gaussian distribution is also shown in FIG. 1 for w=1/2. As can be seen in FIG. 1, Gaussian beams typically provide non-uniform light distribution.

Figure 2:
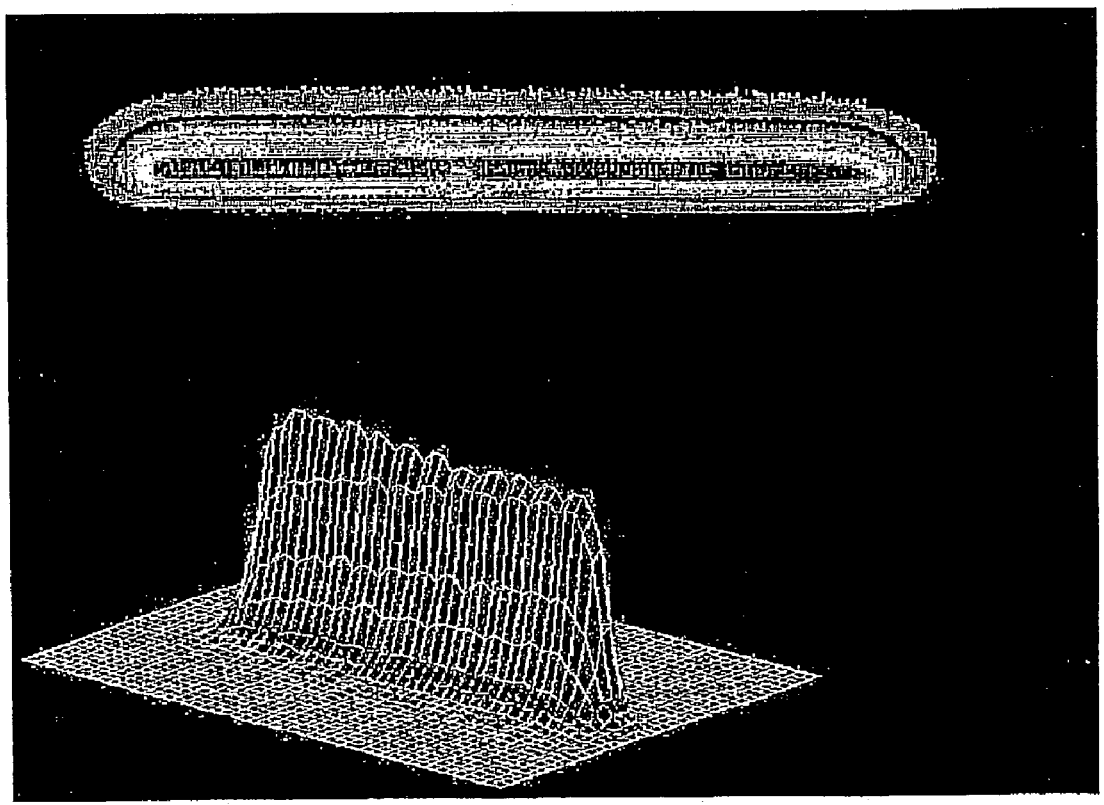
FIG. 2 illustrates a scanning of a Gaussian beam, such as that of FIG. 1, according to some embodiments of the present invention.

Scanning such a Gaussian beam, or a beam with similar properties, may yield results that can be seen with reference to FIG. 2. The plot in FIG. 2, for example, was made by scanning a beam across the face of a Charge Coupled Device (CCD) and recording the integrated intensity. It can be seen in FIG. 2 that such a scan, while relatively smooth, is certainly not a uniform distribution of energy.

A plurality of such scans may be nested together, according to some embodiments of the present invention, to yield a better result. Such an approach to cumulative uniformity is shown in FIG. 3., where 5 scans are placed w apart.

Figure 3:
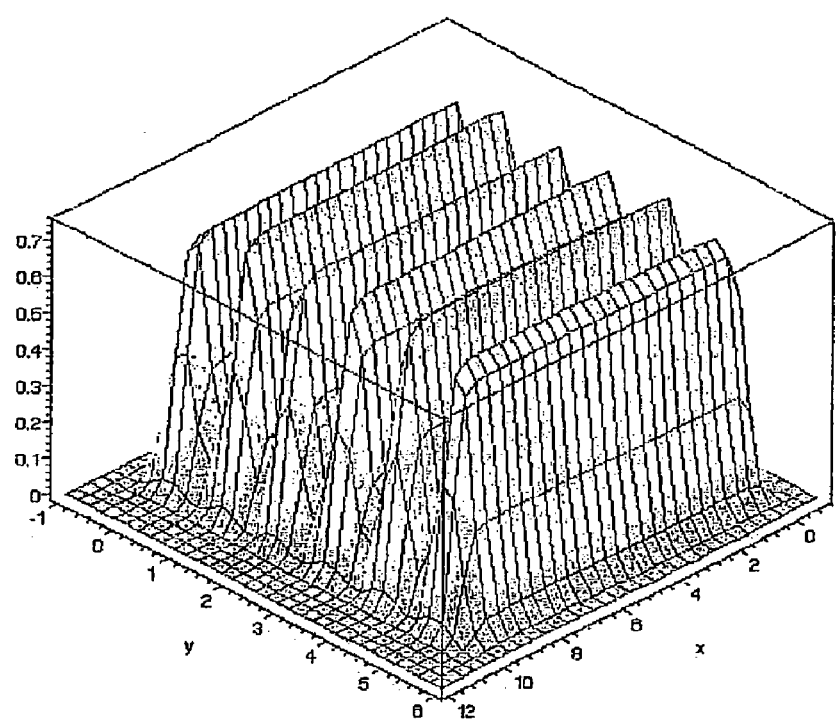
FIG. 3 illustrates a series of Gaussian scans nested together, according to some embodiments of the present invention.
Figure 4:
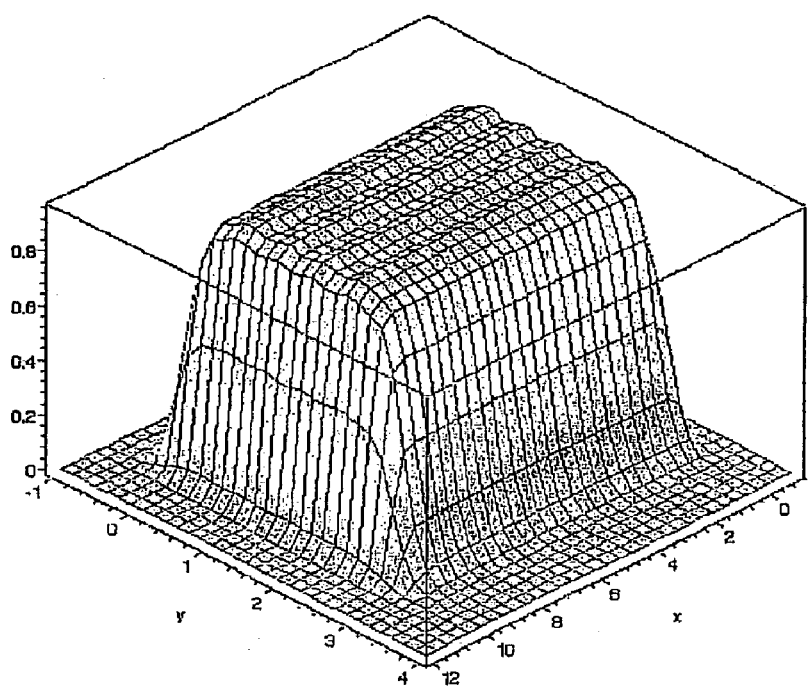
FIG. 4 illustrates the series of Gaussian scans of FIG. 3, packed closer together, according to some embodiments of the present invention.
Figures 5A, 5B, 5C, 5D, 5E:
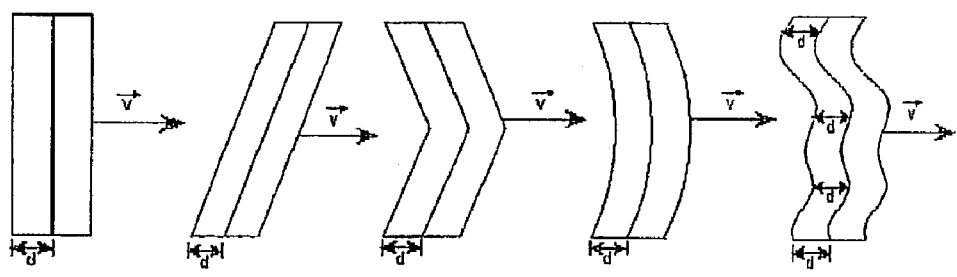
FIGS. 5A-5E illustrate a series of optical waveguides with cross sectional geometries characterized by equidistant edges, according to some embodiments of the present invention.

FIG. 4 illustrates the 5 scans of FIG. 3 placed w/2 apart. It is clear, however, that even though cumulative uniformity may be achieved in this way, such uniformity is not instantaneously uniform.

Usage of Gaussian distributions for defining laser beam intensity profiles may be acceptable when dwell time is not critical, such as in most forms of PDT. However, where dwell time is critical, embodiments of the invention may provide an instantly uniform irradiation. In these "dwell time sensitive" procedures, most or each of the points on the irradiated tissue may "see" the light beam for approximately the same amount of time. The beam may therefore dwell on all of the irradiated tissue for approximately the same duration time. The effects of such uniform dwell time may be to minimize the in-homogeneity of treatment and increase the therapeutic outcome.

Reference is now made to FIGS. 5A-5E, which illustrate a series of cross section shapes for waveguides, according to some embodiments of the present invention. The waveguides used according to some embodiments of the present invention may have regularly shaped cross sections that may generate regularly shaped light beams. These light beams may provide energy that is relatively uniform across the cross sections of the beams. The beams may be combined to accurately cover a selected target surface such that substantially all selected spots or points within the whole irradiated surface or selected portions of the surface may have substantially equal exposure to the energy provided. Alternatively or additionally, all selected spots or points within the whole irradiated target surface or selected portions of the target surface may experience the light beam(s) for substantially the same amount of time (uniform dwell times). Non-limiting examples of such shapes include squares, rectangles, rhombuses, etc. The effects of beams transmitted by such optical waveguides in certain directions may be experienced by (all or selected points within) target tissue (e.g., tissue that receives the beams) as having uniform width in the scanned direction (v), as can be seen in FIGS. 5A-5E.

When using such waveguide shapes, the resulting beams typically have cross-sectional geometries that coincide with the equidistant edges (d) of the spot or shape of the beams, as defined by the scan direction (v). For example, scanning a square spot along its diagonal may not provide uniform illumination but scanning it along an edge may provide uniform illumination. The usage of regularly shaped waveguides may provide efficient use of light since most of the light may be utilized for the scanning purposes, and relatively little light may need to be unutilized. Regular shapes that may be utilized for purposes of providing uniform illumination may not be limited to squares and other basic geometric shapes. Any objects or shapes that have equidistant or approximately equidistant edges (d), as measured with respect to the scan direction, may provide this. For example, uniform illumination may even be provided by the shape beam that maybe transmitted through a waveguide such as that illustrated in FIG. 5E.

Geometrical shapes such as squares and rectangles, for example, may be the most straightforward shapes to generate. Therapies such as MPC, for example, may be served well by scanning using the above waveguide shapes to create uniform treatment where the dwell time on tissue is a critical parameter. This method may be efficient in that most or all of the light is utilized and relatively little if any light is thrown away, aside from some Fresnel losses (reflections at interfaces with different indices of refraction) at the optical surfaces. These losses may be limited or minimized by using suitable coatings, such as an antireflection coating that serves to counteract the mismatch in the indices of refraction between, the waveguide and the air. This may be achieved by taking advantage of the wave nature of light and making a plurality of reflections nominally disappear by destructive interference. Such a method is well known in the art.

Figure 6:
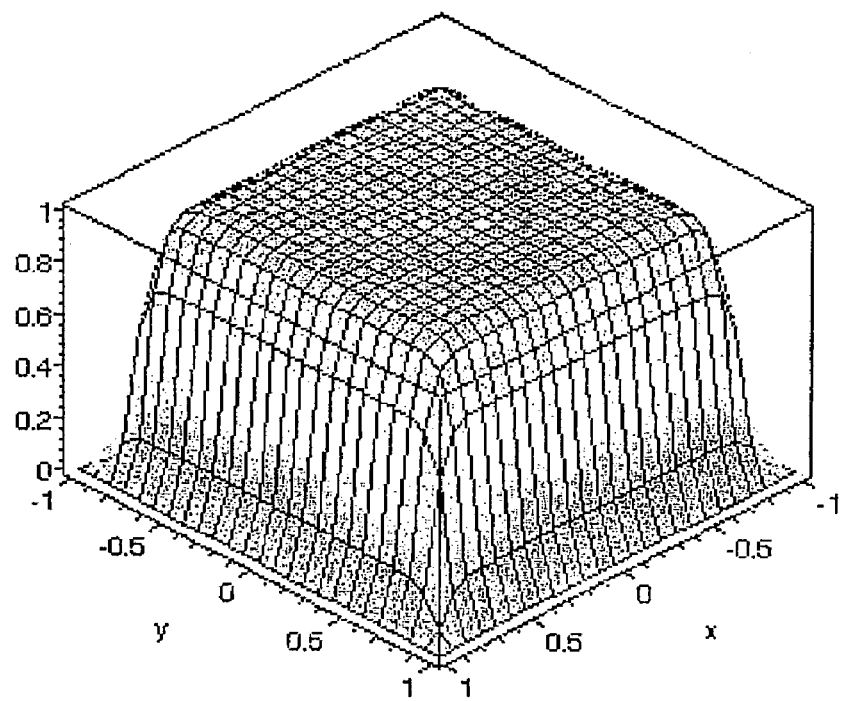
FIG. 6 illustrates an instantly uniform intensity distribution when scanning using a regular geometry such as a square, according to some embodiments of the present invention.

Reference is now made to FIG. 6, which illustrates energy distribution when radiating laser beams using waveguides of regular geometric shapes, according to some embodiments of the present invention. A regular geometry, for example a rectangle or square, may be used to provide an instantly uniform intensity distribution, as shown in FIG. 6.

Figure 7A:
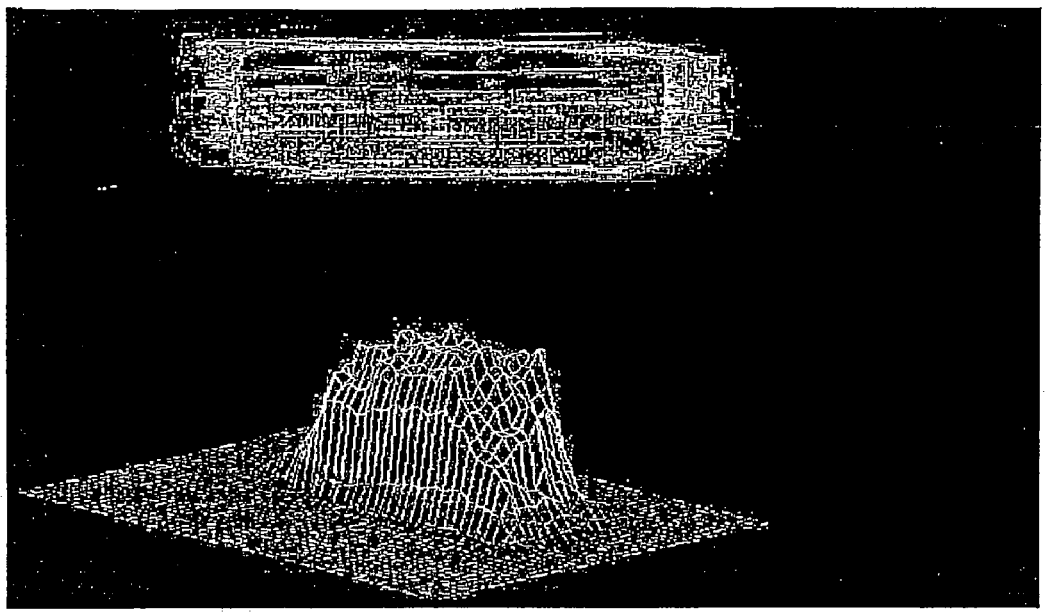
FIG. 7A illustrates the possible edge effects when a scan is implemented using optical designs with non-smoothed edges, according to some embodiments of the present invention.
Figure 7B:
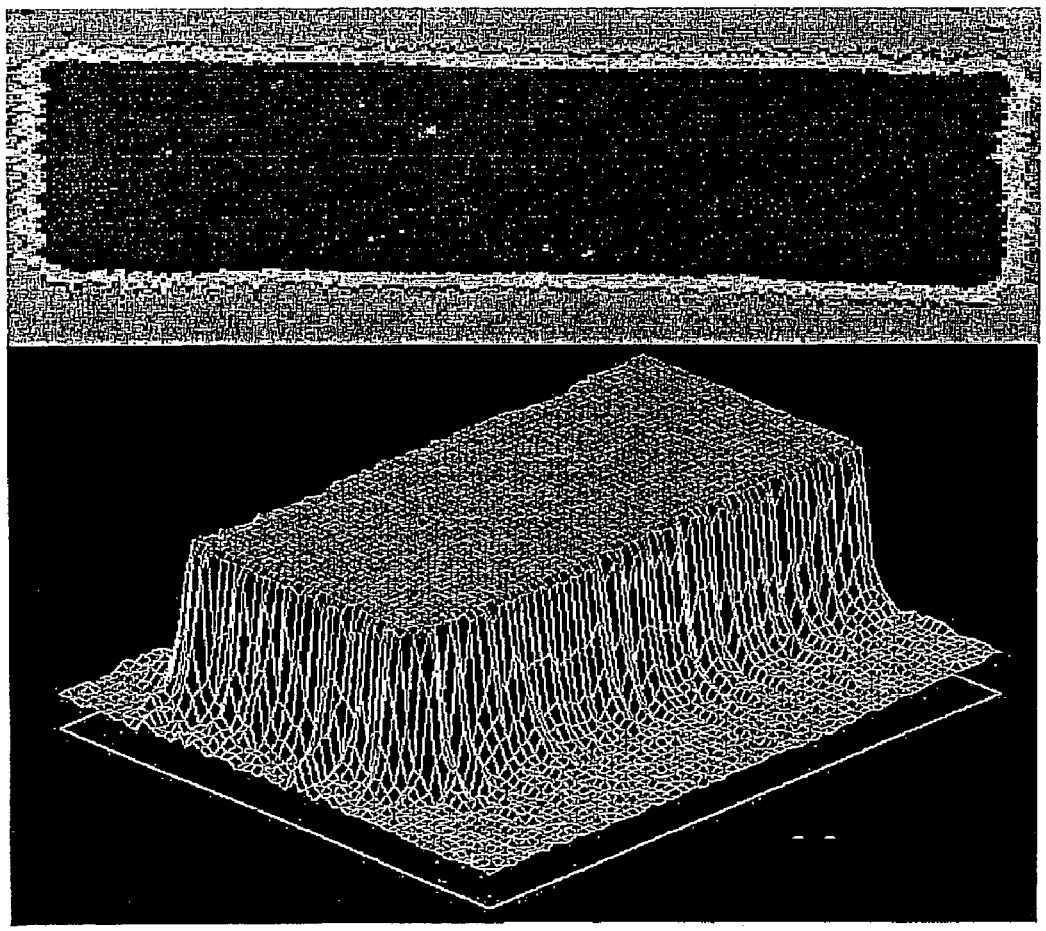
FIG. 7B illustrates the possible edge effects when a scan is implemented using optical designs with smoothed edges, according to some embodiments of the present invention.

As can be seen in FIG. 7A, when scanned, the energy distribution shown above may yield some scan end effects where the scanner accelerates. However, by scanning across a parallel pair of hard edges (such as an open window, for example), to smooth or clip off the ends of the scan, these effects may be significantly reduced and the scan may be made relatively constant and uniform. This smoothing and/or clipping process may be equivalent to removing the areas where the scanned beams have a greater or lesser illumination density. An example or results of a scan using an optical waveguide with smoothed or clipped edges may be seen with reference to FIG. 7B. As can be seen in FIG. 7B, the edge effects of a scanned image may be minimal, and providing a significant degree of uniformity in the illumination provided by such a scan.

According to some embodiments of the present invention, a "uniformity aperture" may be placed in front of the waveguide's exit face to enhance the uniformity by clipping the rolling edges of the beam. Such a result may be used when dosimetry is important, and to provide an approximately uniform dwell time, as can be the case, for example, in PC and SRT. Because PDT typically involves photochemistry, it may have relaxed requirements for dwell times, but accurate dosimetry may still be required. The same may be true for diagnostic imaging, where it is primarily the integrated irradiance at the sensor that forms an image.

According to some embodiments of the present invention, light beams that are radiated using geometric shaped wave guides may be limited by time constants, such that the target tissue may be exposed to the beam for a specific (typically cumulative) time. The beam, emanating from a continuous wave (CW) laser source, for example, may move continually around the target surface, or selected portions of the target surface, until the target time has been reached thereby enabling uniform dwell time for target all or selected points, such as cells, precisely according to the amount of time that is determined.

According to some embodiments of the present invention, an apparatus and method are provided that enable the provision of uniform exposure to targeted points, such as cells in, for example, the Retina of the eye. Accordingly, light within a fiber optic cable may be coupled into light guide or waveguide, which may have, for example, a regular cross-section. A beam exiting the waveguide may be of a regular shape, thereby enabling uniform illumination of target tissue, with uniform dwell times being achievable for each point on the target tissue. The beams may subsequently be scanned by laser scanning apparatus with a desired aspect and magnification onto, for example, a retina, such that the pivot point of the beam penetrates through the iris. An apparatus and method for scanning such light beams onto the retina is shown with reference to FIG. 8A, but other apparatuses and methods may be used.

Figure 8A:
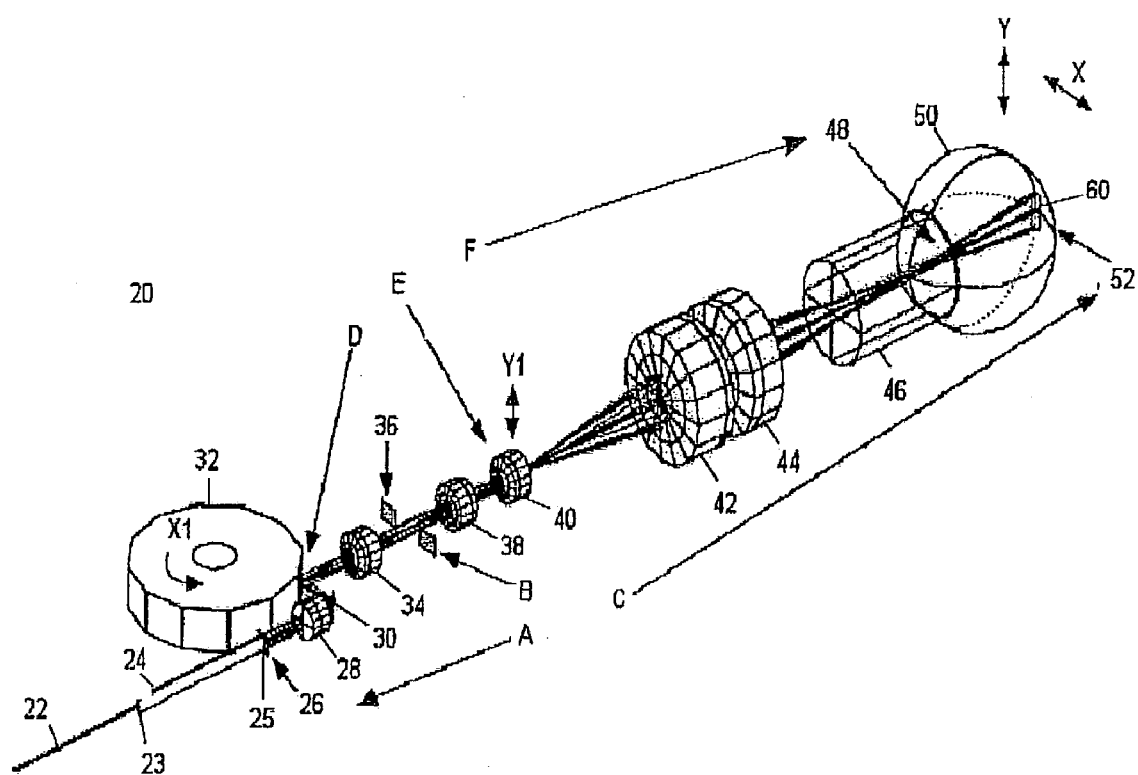
FIG. 8A illustrates an apparatus, according to some embodiments of the present invention, for producing uniform illumination.

As can be seen in FIG. 8A optical system 20 may provide at least one beam 60 of light at the back 52 of the eye 50. The direction of beam 60 may be altered by moving the beam, for example, in directions X and Y. The control over beam 60 may enable, for example, rapidly scanning in a direction X, then stepping or scanning more slowly in the direction Y. By alternating between fast and slow modes of scanning, for example, the entire back of the eye may be exposed, if needed, while avoiding excess irradiation. Such a scanning method may encompass, for example, raster scanning or any other suitable scanning method, wherein, for example, the slower scanning may be done without irradiating the tissue. Such an imaging method may thereby enable the scan to pivot around the pupil of the eye and completely cover the retina. According to some embodiments of the present invention, the output of the scanned light may be modulated (with an acousto-optic scanner, for example) to illuminate only certain areas or regions, such as might be the case for SRT where it to be beneficial to leave untreated areas between the treated areas to assist the wound healing process. A method to achieve uniformity of the exposure is described below. Other scanning patterns or methods may be used, using any number of directions and/or any number of scanning speeds etc.

Figure 8B:
FIG. 8B illustrates an example of a "gated" windowing aperture, as compared to a standard windowing aperture, according to an embodiment of the present invention.
Figure 8B:

Optical system 20 may receive light via a fiber optic cable 22 which may have, for example, a circular cross-section, although other cross sections may be used. The light within fiber optic cable 22 may be coupled into one or more light guides or waveguides 24, which may have, for example, regular cross-sections, such as a rectangular cross section. In this example, two waveguides 24, for example, may be butt-coupled. Alternatively, at least one "regular fiber" may be used, and/or at least one lens may be used to get light into the regular fiber thereby avoiding butt coupling. According to an embodiment of the present invention, the circular diameter of fiber 22 is approximately 365 µm and the rectangular dimensions of light guide 24 are approximately 2 mm in the Y dimension and 0.4 mm in the X direction. Of course, this is only one example, and both smaller and larger fibers and waveguides may be used, depending upon the specific need. The X and Y directions may be oriented as shown by labels X and Y in FIG. 8. For efficient butt coupling, the rectangular dimensions of the waveguide 24 typically exceed the diameter of the circular fiber, but other configurations and methods may be implemented. It is understood that coupling between the waveguides may be achieved by other means such as the use of lenses.

Waveguide 24 may be used to convert the possible non-uniform irradiance pattern at the output face 23 of fiber optic 22 into a mostly uniform irradiance pattern with a desired aspect ratio at the output face 25 of the rectangular light guide 24. In order to achieve a reasonable degree of irradiance uniformity, such as, for example, less than a 20% irradiance fluctuation across the output face 25, the length of the rectangular waveguide 24 may exceed the maximum dimension of the output face 25. The specific length of waveguide 24 required depends on the numerical aperture of the light exiting fiber face 23 and upon the degree of uniformity desired at the output face 25. It is generally considered mostly uniform when the length is between at least 5 to 10 times the largest cross-sectional dimension of the, for example, rectangular waveguide. At least one method for determining the required waveguide length can be seen with reference to PCT patent application No. WO 02/076318 A1, by the same inventor, which is hereby incorporated by reference in its entirety.

A uniformity aperture 26, which may be, for example, an adjustable object or a hole of a suitable size and shape etc., may be placed typically immediately following output face 25. This aperture 26 may have dimensions slightly smaller than the output face 25 of the light guide 24 so that aperture 26 is slightly overfilled by the light exiting the output face 25. Aperture 26 may be used to provide enhancement of the uniformity of the irradiance distribution of the light in plane A immediately following the aperture 26, by smoothing the edges of the light beam exiting the output face 25, thereby cleaning up the beam.

The shape of aperture 26 may depend on the irradiance distribution at the output plane 25. For example, if the irradiance distribution at output plane 25 is mostly uniform within the rectangular coordinates defined by waveguide 24 except for, for example, some irradiance roll off near the edges, then aperture 26 may be a smaller scaled rectangle used to clip the unwanted edges. On a more complex level, the shape of the aperture may take on a more complicated shape as outlined in FIGS. 5A-5E. The shape may be dictated by a requirement that the irradiance of the aperture as integrated along the fast scan direction X may be constant as a function of the orthogonal direction Y; such constraints need not be followed, and other constraints may be used. It is important to also note that the sides of this aperture 26 may be made piecewise adjustable. In this way, an arbitrary irradiance distribution may be measured and subsequent adjustments may be made to the aperture to achieve the desired level of uniformity. The uniform aperture may typically have straight edges, but may be of other configurations.

Aperture 26 may be followed by at least lenses 28 and 34. The function of lenses 28 and 34 may be to image the beam exiting the aperture 26 (plane A) to a conjugate plane B. At plane B a windowing aperture 36 may be located. This aperture 36 may serve to remove the endpoints of the scan that may typically be non-uniform, thereby cleaning up the scan. A pupil plane (D) may lie between lenses 28 and 34. A fast scanning device such as rotating polygon 32 may be placed within this plane.

in the case of FIG. 8A, for example, the fast scanning device 32, which may be a rotating polygon mirror or any other suitable scanning device, may rotate in the X1 direction to generate, for example, a fast scan in the X direction in the C plane. The turning mirror 30, for example, of the scanning device 32 may bend the light prior to hitting scanner 32, to provide suitable beam access, such as an L-shaped optical path, to the facet of the rotating polygon 32. The stationary windowing aperture 36 may allow for smooth turn on and turn off of the scanning beam at both the beginning and at the end of the fast scan in the C plane. This may be done by, for example, choosing the number of facets and facet dimensions of the rotating polygon 32 such that the image of the uniformity aperture 26 at plane B is overscanned at the beginning and end with respect to the stationary aperture 36. The conjugate pupil planes may be important for aperturing. The image planes may be important for scanning.

Uniform scanning may typically be performed is a way that allows beams to be able to move uniformly relative to the shape being scanned. This may involve only scanning along the X-axis, and then moving in the Y-direction before another X-axis scan, or vice versa. Note that when used herein the X and Y directions are interchangeable. Further, other scanning patterns and methods and systems for producing scanning patterns may be used. Additionally or alternatively a scheme may be implemented where the waveguide rotates about its axis, and the scanner moves the image of the rotated waveguide according to its orientation.

The windowing aperture 36 may be followed by lenses 38, 40, 42, 44, and 46. Other numbers or types of lenses may be used. One of the overall roles for these lenses may be to provide an image conjugate with the desired magnification of plane B to plane C. Plane C may be located at the back 52 of the eye 50. An additional, or alternate role of the lenses may be to provide pupil conjugates, for example images of the pupil plane D, with the appropriate magnification at planes E and F. Lens 40, which may be translated in the direction Y1, may be placed at, for example, plane E. This lens movement, Y1, may provide scanning in the Y direction in the C plane. This may be considered the step or slow scan direction, and could just as easily be achieved using a different scanning mechanism such as a galvonometer, acousto-optic deflector, rotating wedge, and/or hologon, etc. The optical subsystem, including lenses 34, 38, 40, 42, 44, and 46 may create conjugate images of the pupil planes D, E, F. Plane F may coincide with, for example, the iris 48 of the eye 50. By imaging planes D and E to plane F and by placing the scanning mechanisms 32 and 40 in those planes, the pivot point for the scanning beam may be located at the iris 48. This may allow for minimal clipping of the beam by the iris of the eye as the beam is scanned, and may minimize the affect to the optical power caused by the lens of the eye. Lens 46 may be, for example, a corneal contact lens, which may effectively neutralize the optical power of the cornea. In alternate embodiments, the speeds of the two scanning directions need not differ, and other scanning patterns, for example not using two directional devices, may be used.

Optical system 20 may include, for example, a modulator for restricting a scan to at least one selected area of a target. Such a modulator may be located on the input side of the optical fiber 24, or at any other suitable place to, for example, temporally gate the beam. The modulator may also be implemented by using a more structured fixed aperture (such as a comb-like structure, for example) located at, for example, the windowing aperture, to spatially gate the scanned beam. Such an implementation, as can be seen with reference to FIG. 8B may, for example, serve to provide irradiation to selected portions of the image plane. This may be useful so as to have treated areas surrounded by untreated areas, as may be important to therapies such as SRT. This may also be accomplished using, for example, a liquid crystal optical phase array, or other addressable devices that may be reprogrammed to provide a variety of different aperture geometries. Usage of a modulator may be indicated by a scan result wherein certain areas of irradiation may be missing.

In the embodiment described in FIG. 8A, lenses 28, 34, 38, 40, 42, 44, 46, along with the eye 50 may generate an image of the light beam exiting the uniformity aperture 26 onto the windowing aperture 36 and to at least one portion of the back of the eye 52. These image planes are referred to as planes A, B, and C in the figure. These lenses may also provide conjugate pupils at planes D, E, and F. At two of these pupil planes, E, F, scanning devices may be placed so as to provide multiple scan parameters, such as fast and slow scan directions, for example. The plane F may be the iris 48 of the eye 50. The fast scan device may be a spinning polygon mirror 32, or any other suitable device, and the slow scan device may be a translating lens 40, or any other suitable device. Uniformity and beam shaping may be achieved through the use of the fiber input 22, the regular waveguide 24, and the uniformity aperture 26. The fast and slow scan devices may be reversed, or alternative components or sets of components may be used.

Figure 9:
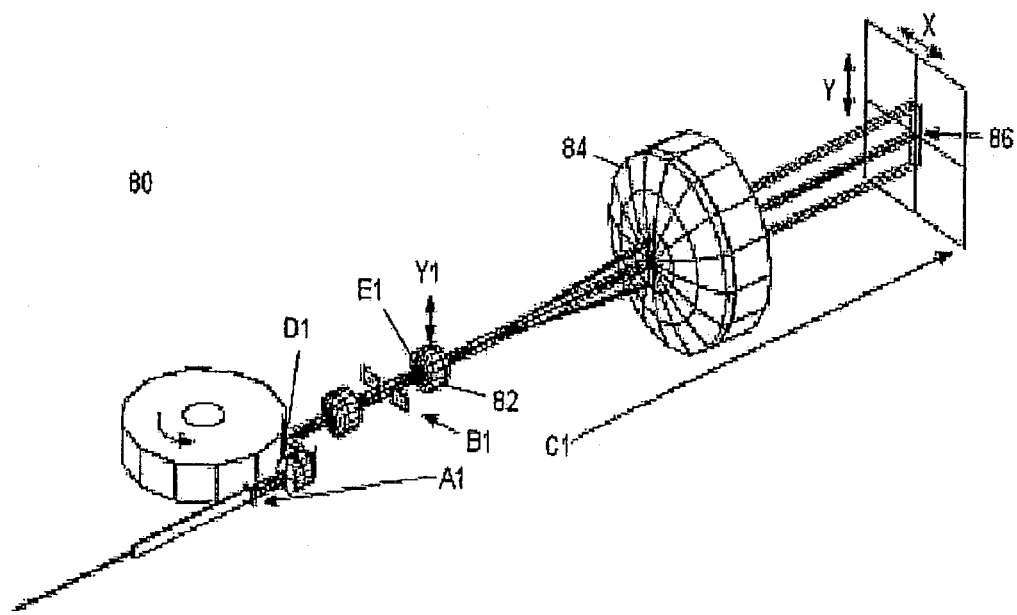
FIG. 9 illustrates an alternative apparatus, according to some embodiments of the present invention, for producing uniform illumination.

A simplified optical system, according to some embodiments of the present invention, may be used when a scanned uniform irradiance distribution is required, without the presence of an eye. As can be seen with reference to FIG. 9, optical subsystem optionally including lenses 82 and 84 may replace lenses 38, 40, 42, 44, 46 and the eye 50 of FIG. 8. This lens system may be simpler than that illustrated in FIG. 8 because there may be no need to pivot the scan beam about the iris. In FIG. 9, the fast scan may be accomplished using a spinning polygon mirror 84 or any other suitable scanning component(s), and the slow scan may be accomplished, using lateral displacement (e.g., translation) Y1 of lens 82. However, these scans may also be achieved using galvanometers, acousto-optic deflectors, moving lenses and/or wedges, and holograms, etc. The uniformity aperture may be in plane A1. Planes A1, B1, and C1 may be image conjugates with the appropriate magnification. The plane C1 may be the plane of the uniform scan with the stationary beam 86 as shown. There may be no need to image the pupil planes or the scan planes D1 and E1 to be coincident. There may also be no need in general for the scanning beam to be telecentric, although this may be achieved through the appropriate optical design.

Figure 10:
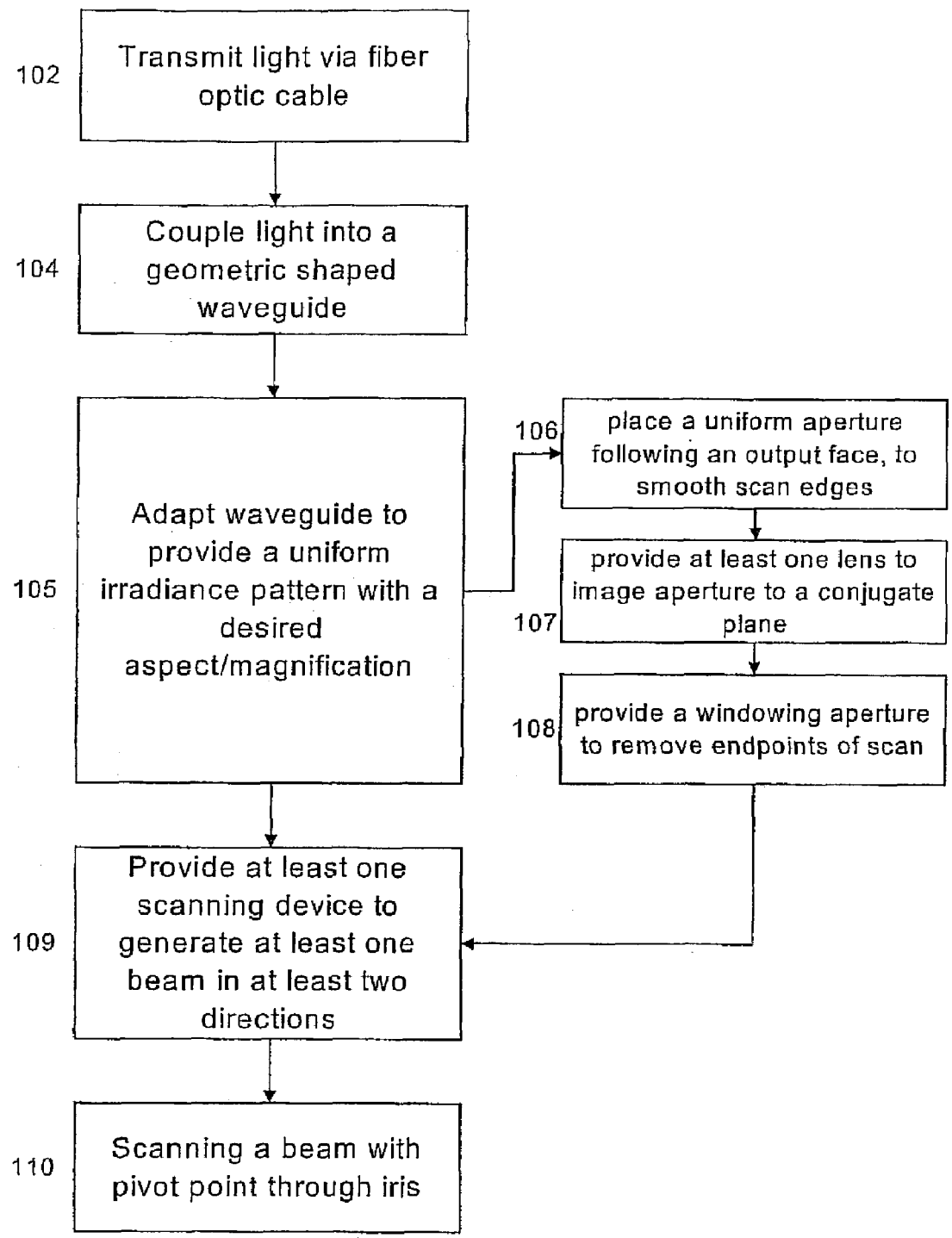
FIG. 10 is a flow chart illustrating a method of uniform illumination, according to some embodiments of the present invention.

A method for implementing uniform illumination, according to some embodiments of the present invention, may be seen with reference to FIG. 10. As can be seen in FIG. 10, in step 102 light may be transmitted via, for example, a fiber optic cable. In step 104, the light may, be coupled into a regular shaped waveguide. In step 105, the waveguide may be subsequently adapted to provide a uniform irradiance pattern with a desired aspect/magnification (as described above). The provision of such uniform irradiance may require steps including placing a uniformity aperture following an output face 106, to smooth scan edges. Following this at least one lens may be provided to image the aperture filtered image to a conjugate plane 107. Additionally, a windowing aperture may be provided to remove endpoints of a scan 108. In step 109 at least one scanning device may be provided to generate at least one beam in at least one direction. In step 110, scanning may be implemented by a beam with the beam's pivot point penetrating the iris or any other selected area. In other embodiments, other steps, and other series of steps, may be used.

Figure 11:
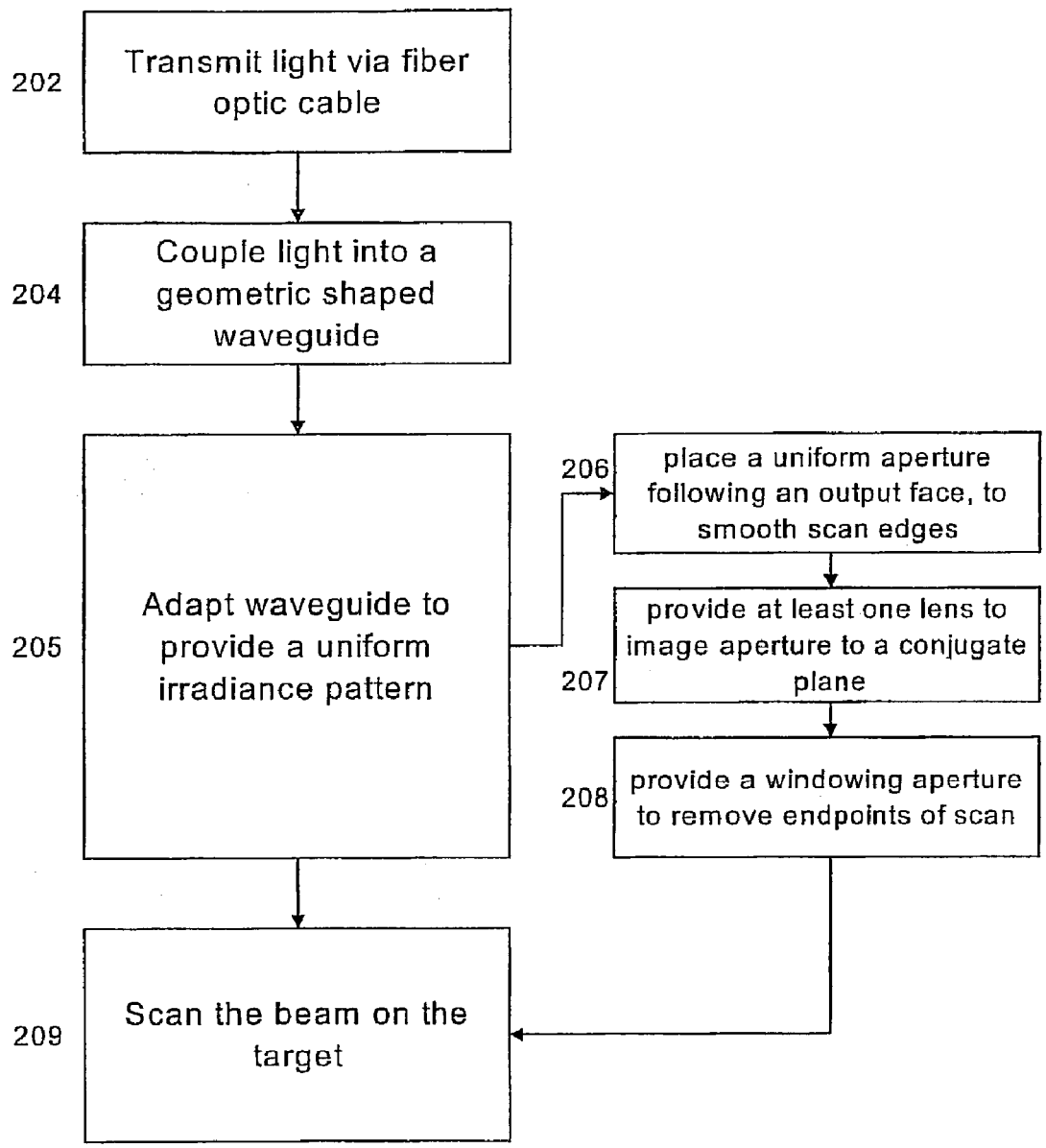
FIG. 11 is a flow chart illustrating a method of uniform illumination, according to some embodiments of the present invention.

A method for implementing uniform illumination, according to some embodiments of the present invention, may be seen with reference to FIG. 11. As can be seen in FIG. 11, in step 202 light may be transmitted via, for example, a fiber optic cable. In step 204, the light may be coupled into a geometric shaped waveguide. In step 205, the waveguide may be subsequently adapted to provide a uniform irradiance pattern (optionally with a desired aspect/magnification). The provision of such uniform irradiance may require steps including placing a uniformity aperture following an output face 106, to smooth scan edges. Following this at least one lens may be provided to image the aperture filtered image to a conjugate plane 207. Additionally, a windowing aperture may be provided to remove endpoints of a scan 208. In step 209 at least one scanning device may be provided to generate and transmit at least one beam to the target. In other embodiments, other steps, and other series of steps, may be used.

According to some embodiments of the present invention, PhotoDynamic Therapy (PDT) may be performed. Unlike PC, PDT may involve, for example, an exogenous chromophore, which is a drug that changes oxidative state upon exposure to light of the appropriate wavelength. This form of the drug may be selectively retained by the target tissue and, like chemotherapy, attempts to destroy the offending tissue while sparing the healthy portions. The dosimetry is often, largely unknown in PDT. Some embodiments of the present invention may yield a well-defined area of uniform irradiance, and therefore lend themselves well to regulated PDT.

According to some embodiments of the present invention, diagnostic applications may be implemented. Imaging with uniform illumination may yield better results than imaging using non-uniform illumination.

It will be appreciated that additional embodiments of the present invention may be implemented using pulsed laser sources. Additional embodiments of the present invention may also be implemented on various target materials, tissues etc., and may be integrated into procedures including but not limited to ophthalmic procedures, cosmetic procedures, surgical procedures, dental procedures and alternative personal or industrial procedures etc.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method of performing a procedure selected from the group consisting of photocoagulative treatment, microphotocoagulative treatment, photodynamic therapy and illumination for imaging, the method comprising:
    coupling a laser beam into at least one optical waveguide with a regularly shaped cross section;
    adapting said waveguide to provide a uniform illumination pattern; and providing at least one scanning device to scan said uniform illumination pattern on at least a portion of the target, wherein said scanning comprises:
    moving at least one beam of light in at least a first direction according to at least a first speed;
    moving at least one beam of light in at least a second direction according to at least a second speed; and
    alternating scanning between at least said first direction and at least said second direction.

2. The method of claim 1, wherein said uniform illumination provides uniform dosimetry to at least a Portion of points on the target surface.

3. An apparatus for irradiating a target with immediate uniform illumination, the apparatus comprising:
    a continuous wave laser source;
    at least one optical waveguide with a geometrically shaped cross section adapted to transmit at least one light beam from said continuous wave laser source in a uniform illumination pattern;
    at least one modulator for restricting said beam to selected areas of the target; and
    at least one scanning device to scan said beam to the target, such that substantially selected target points are irradiated with substantially uniform dosimetry of said beams.

4. A method to enable uniform dwell time on a target, the method comprising:
    providing a continuous wave light beam via a waveguide with a regularly shaped cross section;
    smoothing the edges of said light beam;
    scanning said light beam in a pattern so as to provide instantaneous uniform illumination of at least a portion of the target, wherein said beam irradiates the retina; and
    removing the endpoints of said light beam;
    wherein said uniform illumination provides uniform dosimetry to selected points on the target surface.

5. A method to enable uniform dwell time on a target, the method comprising:
    providing a continuous wave light beam using laser beam generating means;
    transmitting said light beam through a waveguide with a regularly shaped cross section;
    smoothing the edges of said light beam;
    passing said light beam through a gated window aperture; and
    scanning said light beam in a pattern so as to provide instantaneous uniform illumination of the target.

* * * * *

UNITED STATES PATENT AND TRADEMARK OFFICE
CERTIFICATE OF CORRECTION

| | |
|---|---|
| PATENT NO. | : 7,263,255 B2 |
| APPLICATION NO. | : 10/408783 |
| DATED | : August 28, 2007 |
| INVENTOR(S) | : Dan E. Andersen et al. |

It is certified that error appears in the above-identified patent and that said Letters Patent is hereby corrected as shown below:

Claim 2 at Column 11, lines 26-28 delete: "The method of claim 1, wherein said uniform illumination provides uniform dosimetry to at least a Portion of points on the target surface."

and should read: --The method of claim 1, wherein said uniform illumination provides uniform dosimetry to at least a portion of points on the target surface.--

Signed and Sealed this

Fifteenth Day of April, 2008

JON W. DUDAS
*Director of the United States Patent and Trademark Office*